United States Patent [19]

Döbert

[11] Patent Number: 4,756,014

[45] Date of Patent: Jul. 5, 1988

[54] DENTAL X-RAY DIAGNOSTICS INSTALLATION

[75] Inventor: Michael Döbert, Lorsch, Fed. Rep. of Germany

[73] Assignee: Siemens Aktiengesellschaft, Berlin and Munich, Fed. Rep. of Germany

[21] Appl. No.: 942,800

[22] Filed: Dec. 17, 1986

[30] Foreign Application Priority Data

Dec. 20, 1985 [DE] Fed. Rep. of Germany ....... 3545487

[51] Int. Cl.$^4$ ............................ A61B 6/14; H05G 1/02
[52] U.S. Cl. ........................................ 378/039; 378/40; 378/184
[58] Field of Search ..................... 378/38, 39, 40, 184, 378/21, 27, 24, 25, 181, 182

[56] References Cited

U.S. PATENT DOCUMENTS

| | | | |
|---|---|---|---|
| 2,565,378 | 8/1951 | Land | 378/182 |
| 4,034,225 | 7/1977 | Hudson et al. | 378/39 |
| 4,228,356 | 10/1980 | Cushman | |
| 4,286,161 | 8/1981 | Hozumi | 378/38 |

FOREIGN PATENT DOCUMENTS

| | | |
|---|---|---|
| 3005203 | 8/1980 | Fed. Rep. of Germany . |
| 3304061 | 8/1983 | Fed. Rep. of Germany . |
| 3345208 | 6/1984 | Fed. Rep. of Germany ...... 378/182 |
| 3434369 | 4/1985 | Fed. Rep. of Germany . |

OTHER PUBLICATIONS

Sales Brochure, "Minimize X-Ray Dosage, Maximize Image Quality . . . ", Siemens AG WS11843.

*Primary Examiner*—Craig E. Church
*Assistant Examiner*—T. N. Grigsby
*Attorney, Agent, or Firm*—Hill, Van Santen, Steadman & Simpson

[57] ABSTRACT

An x-ray diagnostic installation for producing panoramic tomograms of the jaw of a patient utilizes a flexible film cassette instead of a rigid film cassette. The film cassette is driven by an electromotive drive arranged in a housing of a film cassette holder behind a secondary diaphragm as seen in the direction of the radiation from a source of radiation. The drive is formed from by at least one drive element, and at least one cooperating element arranged thereto at a distance therefrom with means biasing at least one of the elements towards the other to produce a frictional engagement of the film cassette and move it past the secondary diaphragm.

10 Claims, 4 Drawing Sheets

DENTAL X-RAY DIAGNOSTICS INSTALLATION

BACKGROUND OF THE INVENTION

The present invention relates to a dental x-ray diagnostic installation for panoramic tomograms comprising an x-ray source and a holder for a film cassette. The diagnostic device has a common carrier on which the x-ray source is mounted opposite the holder and the carrier moves around the subject by means of a first adjustment mechanism. The film cassette holder has a second adjustment mechanism for moving a film cassette relative to the radiation source during the exposure as well as relative to a slotted diaphragm arranged in the beam path between the source and the film contained in the cassette.

A known apparatus of a dental x-ray diagnostic device is an ORTHOPANTOMOGRAPH 10, which is disclosed in a brochure entitled "Minimize X-Ray dosage Maximumize image quality" WS11843. In the device of this type, the film is inserted into a roughly hemispherically shaped metal cassette and this rigid cassette is then inserted into a holder connected to the carrier. During the exposure, the film cassette is then adjusted relative to the radiation source via a suitable mechanical control means, for example, via cam plates or the like.

In German OS No. 30 05 203, a device is disclosed in which a straight line rigid film cassette is provided instead of the curved film cassette and the cassette is displaced around the subject together with a film cassette holder in accordance with the movement of the radiation source by means of a separate drive. To this end, a slide rail on which a motor driven roller can roll is arranged in the film cassette holder in accordance with the direction of movement of the cassette and the film cassette holder is fashion box-like. A strip-shaped, slide member extends essentially parallel to the slide rail and is seated within the film cassette holder. The motor is driven so that the movement of the holder and film cassette are synchronized with the movement of the x-ray source upon rotation of a swivel arm with the holder and film cassette being continuously displaced in a longitudinal direction of the slide rail.

Rigid film cassettes are first structurally involved and thus increase costs. In addition, there is a disadvantage in manipulation, particularly because the film to be exposed must be inserted into the cassette in a dark room before every exposure. Such a manipulation is especially involved and time consuming, particularly when a plurality of exposures are to be made in succession. Keeping a plurality of prepared cassettes on hand is frequently impossible for reasons of space as well as cost. Size as well as the weight are therefore disadvantages of such a rigid film cassette. In addition, the weight of the film cassette and of the film cassette holder has a disadvantageous effect on the design of the overall drive. The structural size of the cassette and holder has a disadvantageous effect on the freedom to move the cassette and holder. When positioning the patient's head for preparation of the exposure, the film cassette is disturbingly in the way because of being in the field of vision.

SUMMARY OF THE INVENTION

The present invention is directed to the object of providing an x-ray diagnostic installation wherein the above-mentioned disadvantages are avoided and in which a particularly simple, more cost beneficial structure of the overall film holder can be achieved and the manipulation or handling of the cassette are improved.

To accomplish these goals, the present invention is directed to an improvement in a dental x-ray diagnostic installation or apparatus for panoramic tomograms, said apparatus comprising a radiation source, a holder for a film cassette, a common carrier, said source and holder being mounted opposite one another on the carrier which moves around the subject by means of a first adjustment mechanism, said holder having a slot-shaped opening through which a film cassette is introducable and withdrawable and the holder having means for moving the cassette within the holder relative to the radiation source during the exposure and to a diaphragm with a slot arranged in the beam path between the radiation source and the cassette. The improvements are that the film cassette is a flexible film cassette enclosing the film to be exposed, said means for moving comprising an electromotive drive arranged in the housing of the film cassette holder following the diaphragm as seen in the direction of radiation, said electromotive drive containing resilient means for pressing at least one of the drive members and the cooperating members against the film cassette to cause a friction drive of the cassette by said slot of the diaphragm.

The employment of a flexible film cassette already containing the film to be exposed has only been previously utilized in an apparatus for intraoral exposures, wherein the film cassette is applied to the outside of the patient's mouth and the radiation source is introduced into the patient's mouth so that a transillumination thus occurs from the inside towards the outside for a panorama tomogram. In the present invention, the flexible film cassette allows the overall x-ray diagnostic installation to be designed to be significantly simpler and lighter and in combination with the conveying means which is provided for the film cassette.

The conveying of the film cassette advantageously occurs with the assistance of drive members and cooperating backing members pressing against the cassette and moving it by friction. These are preferably rollers and/or drums which are arranged in a triangular arrangement with a tight spacing and are arranged immediately approximate to the secondary diaphragm and conduct the film cassette so that the inclusion of air between the film and the intensifying foils, which are always currently present per se, can be avoided. Such air inclusions, which lead to smearing of the x-ray image, cannot always be excluded per se given employment of flexible cassettes with intensifying foils because in contrast to the metal cassettes wherein a tensioning of the film and the foil occurs, no tensioning is present in the flexible cassette. With the conveying means proposed in accordance with the present invention, however, intensifying foils and films are placed in tension immediately proximate to the secondary diaphragm and are thus freed of any inclusion of air.

The overall drive is advantageously secured to a carrier, which is removably held in the cassette holder housing as a complete structural unit. In order to improve the servicability, the cassette holder housing is advantageously composed of two halves formed by a longitudinal division of which the one contains or forms a complete drive and the other contains or forms essentially only a secondary diaphragm.

Another advantage can be achieved when in accordance with the further advantageous developments of the invention, the film cassette holder is pivotally arranged around an eccentrically arranged vertical axis advantageously situated at one end of the holder. As the consequence of the pivotability of the film cassette holder, an assistant has a better view while adjusting a patient's head to the proper position corresponding to the intended tomogram. Pivoting of the film cassette holder away from the operating position also has a further, significant advantage that both normal panorama tomograms as well as remote exposures of the skull what are referred to as CEPH exposures can be produced with the one apparatus without structurally involved measures including, among other things, pivoting the x-radiator or other more involved remodelings being required for this purpose.

Other advantages and objects of the present invention will be readily apparent from the following description, drawings and claims.

DESCRIPTION OF THE PREFERRED EMBODIMENTS

Figure 1:
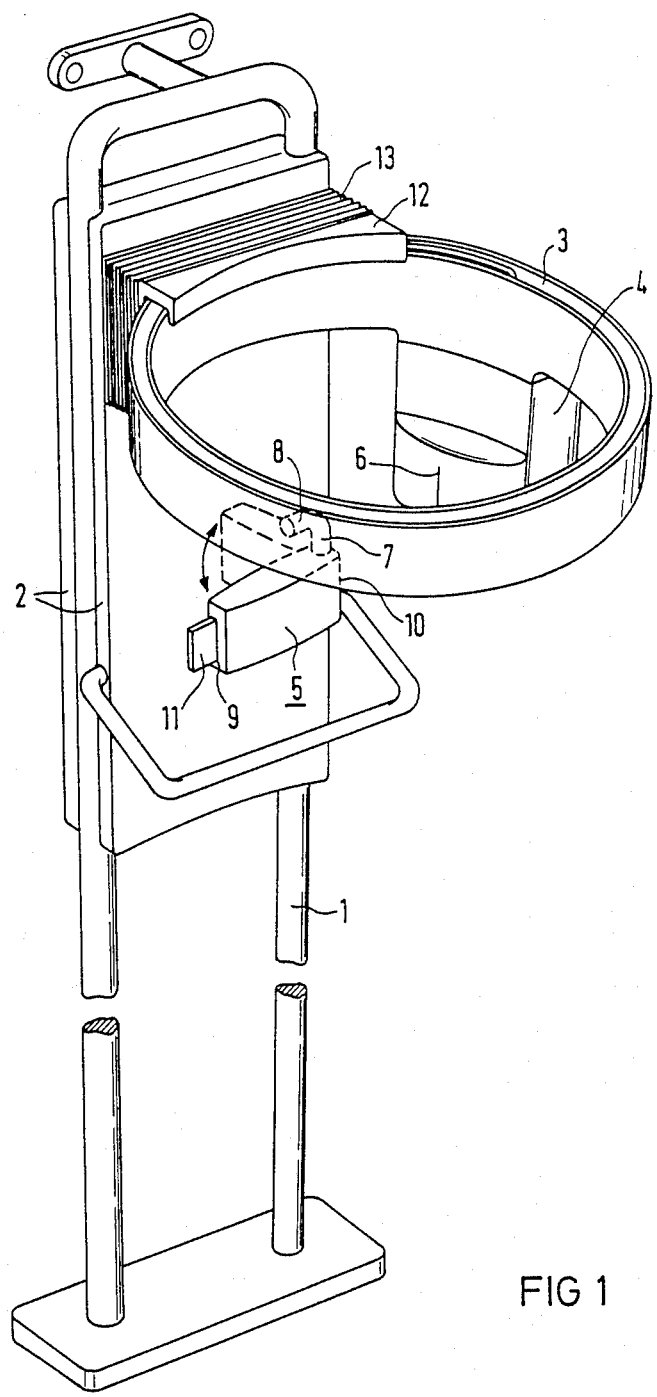
FIG. 1 is a perspective view of an x-ray diagnostic apparatus or installation in accordance with the present invention.

The principles of the present invention are particularly useful in an x-ray diagnostic installation or apparatus for producing panorama tomograms of the jaw of a patient as illustrated in FIG. 1. The apparatus includes a stand 1 formed of two pipes on which a truck or carriage 2 is held in a height adjustable fashion. The carriage 2 carries a turntable ring 3 on which an x-ray source 4 is mounted and a film cassette holder 5 is mounted diametrically opposite to the source. The x-ray or radiation source 4 has a beam exit aperture 6 and is rigidly mounted on the ring 3. The film cassette holder 5 is mounted on an angled carrier arm 8 which has a vertically extending axle or shaft 7 on which the holder 5 is pivotally mounted in the direction indicated by the arrow. The film cassette holder 5 can thus be brought from an employment position indicated with broken lines, which is suitable for tomograms, into a pivoted position indicated in solid lines which first facilitates the position of the patient's head for the assistant and also enables the production of remote exposures that are referred to as CEPH exposures for which the x-ray source of previous apparatus had to be rotated.

On both of its end faces, the film cassette holder 5 contains slot-shaped admission and withdrawal openings 9 and 10, through which a film cassette 11 can be introduced, or respectively withdrawn after the exposure has been produced. The film cassette 11 is a flexible film cassette provided with intensifying foils as is fundamentally employed for the forementioned intraoral exposures. The transport of the film cassette occurs by means of a drive means 40 (FIG. 2) which shall be set forth in greater detail in FIGS. 6 and 7.

To rotate the turntable ring 3 carrying the x-ray or radiation source 4 and the film cassette holder 5, an adjustment mechanism or drive is provided. As illustrated, the turntable ring 3 is a closed ring which is rotatably seated in a bearing or support part 12 and is also pivotally seated therewith relative to the carriage 2. The adjustment mechanism set forth in greater detail herein below is covered by an accordion bellows 13 (FIG. 1) which extends between the truck 2 and the turntable 3.

Figure 2:
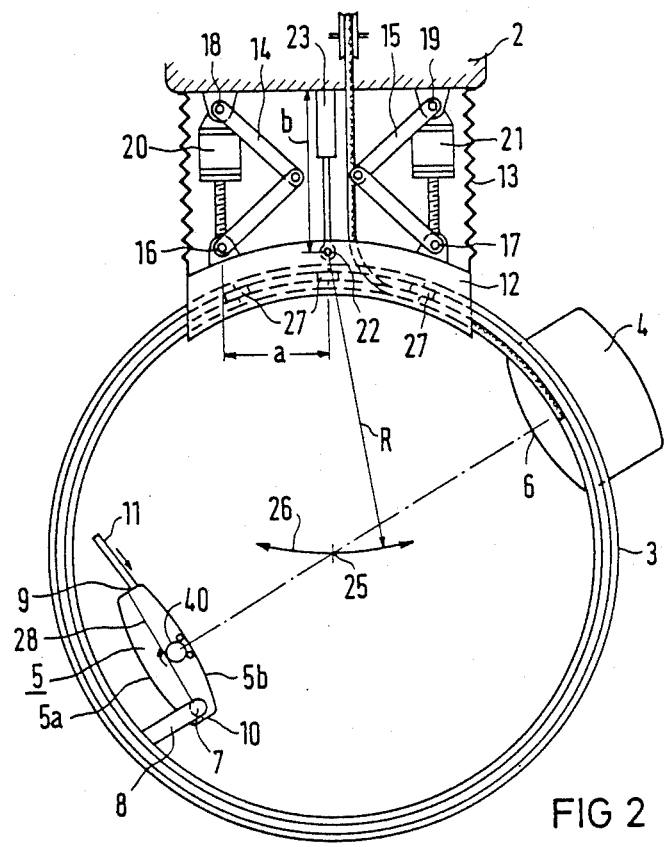
FIG. 2 is a plan view of the apparatus of FIG. 1 illustrating the adjustment mechanism for the carrier of the radiation source and film cassette holder.
Figure 4:
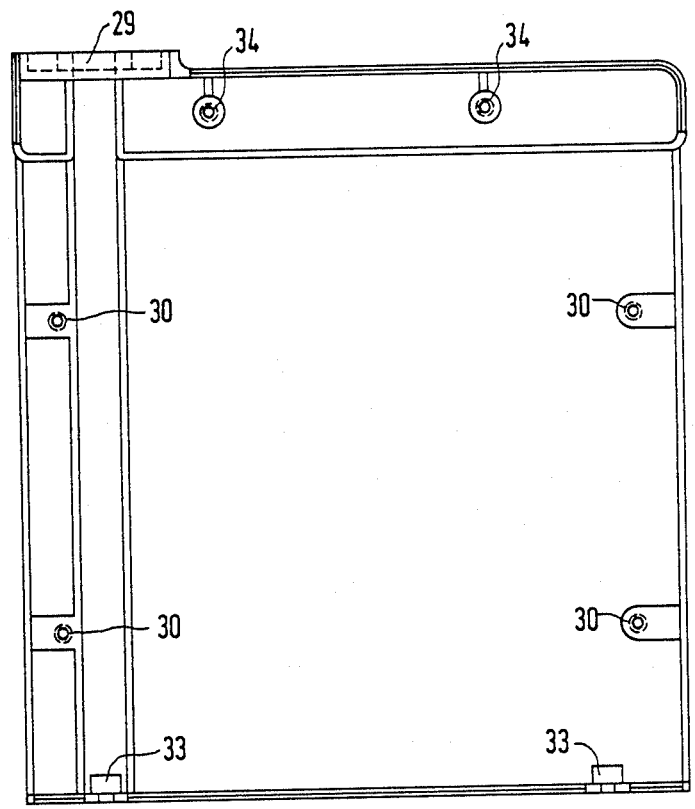
FIG. 4 is a plan view of the half-housing of FIG. 3.

As illustrated in FIG. 2, the support or bearing part 12 is pivotally connected by two pairs of scissor arms 14 and 15 to the carriage 2. As illustrated, one pair 14 is connected by a pivotal connection 16 to the part 12 and by a pivotal connection 18 to the carriage. In a similar manner, the other pair of scissor arms 15 is connected to the part 12 by pivotal connections 17 and to the carriage by a pivotal connection 19. Electrically driven spindle drives 20 and 21 are provided between the pivotal connections with the drive 20 extending between the connections 16 and 18 and the drive 21 between the connections 17 and 19. These spindle drives 20 and 21 are capable of being individually driven by a control means (not shown). Between the two pivotal connections 16 and 17 at a spacings a, the bearing part 12 is pivotally connected to one end of a telescoping arm 23 to form a swivel axis 22. The other end of the telescoping arm 23 is rigidly secured to the truck or carriage 2. In combination with the above described pairs of scissor arm structure, it is possible to displace the turnable ring parallel to the truck 2 by means of appropriate control of the two electrical spindle drives 20 and 21 at the same rate of speed. In addition, it is possible to swivel the ring around the axis 22 by using non-identical displacement of the two drives. This swivelling will cause a center 25 of the ring 3 to execute a transverse motion of about plus or minus 40 mm with the motion being on an arc referenced by arrow 26 having a radius R of approximately 350 mm. To rotate the ring 3 on its axis 25 to form an autorotation motion, the adjustment mechanism includes a drive and two guide rollers 27 which are arranged in a triangular configuration such as with the drive roller between the two guide rollers and engaging an upper edge of the ring 3 as the guide rollers engage the bottom edge of the ring. By controlling the rotation of the ring, as well as the swivelling of the ring, a motion sequence which is achieved in known apparatus for panoramic tomograms can be achieved without requiring the relatively complicated structure of the previously known devices.

As mentioned hereinabove, the drive and guide rollers are arranged so as to engage both the upper and annular edges of the ring 3 and form a triangular arrangement. Expediently, the drive roller is provided in the center to engage an upper edge and the guide rollers are provided on both sides and engage the under or lower edge. For this purpose, the bearing part 12 is fashioned appropriately in a section of a circle with a radius of the ring 3.

Figure 3:
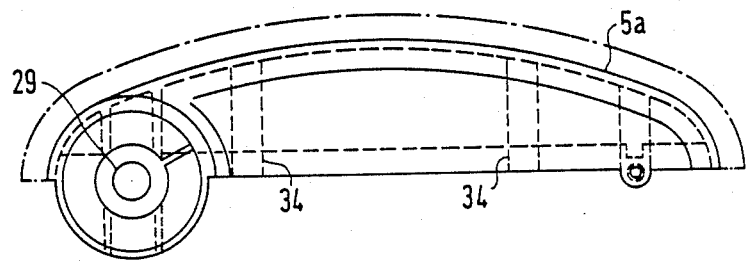
FIG. 3 is an end view of one half of a housing of the film cassette holder.

The film cassette holder 5 is composed of two halves 5a and 5b which are separated from each other along a longitudinal division line 28 (FIG. 2). Enlarged views of the half 5a is shown in FIG. 3, while an enlarged view of the half 5b is shown in FIG. 5.

The one housing half 5a, which faces away from the radiator 4 contains first a bearing bushing 29 (FIG. 3) for the acceptance of an axel bearing on the axis 7 which is required to pivotally mount the holder on the carrier arm 8. In addition, the housing 5a contains four fastening devices 30 for a carrier part 35 shown in greater detail in FIGS. 6 and 7 which accept the drive means 40 of FIG. 2 for driving the film cassette 11.

Figure 5:
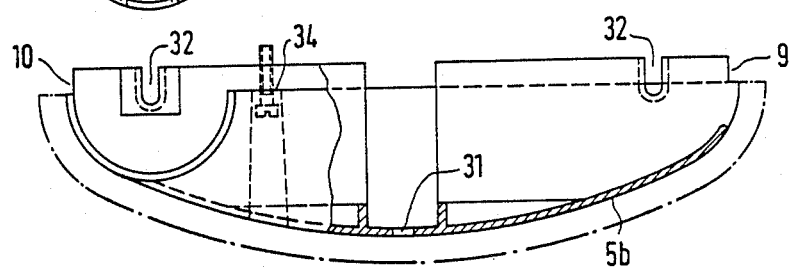
FIG. 5 is an end view with portions broken away of the other half of the housing which coacts with the half of FIG. 3.

The second half 5b, as illustrated in FIG. 5, contains only a secondary diaphragm 31 which is here preferably a component part of the film cassette holder housing itself. For this purpose, at least this housing half 5b is composed of a zinc diecasting, which is especially well suited for the absorption of scattered radiation. For the purpose of assembling the housing halves 5a and 5b, a longitudinal slot 32 which engages into a corresponding peg or projection 33 of the other housing half 5a is provided in the housing part 5b. Over and above this, screw type connection elements are provided at both of the housing halves at the locations such as 34 to hold the two halves together in their assembled condition. The forementioned slot openings 9 and 10 for the introduction as well as the removal of the film cassette are also formed in the two end faces of the housing parts.

Figure 6:
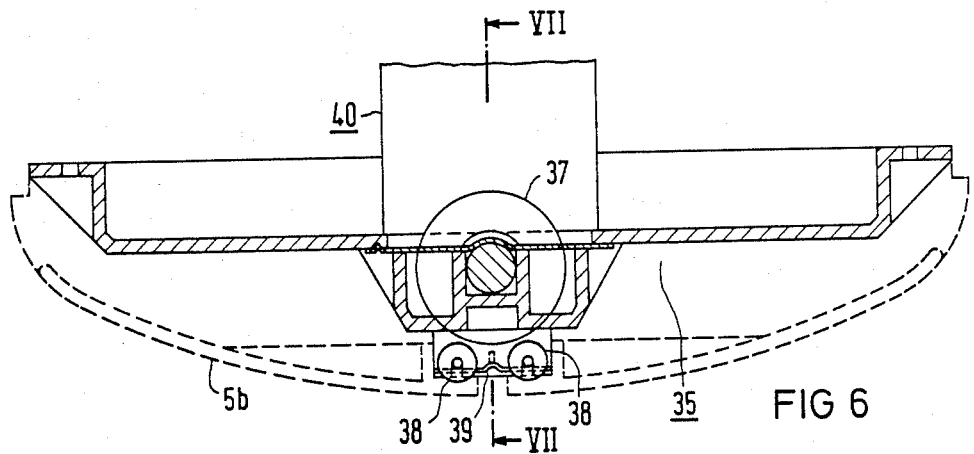
FIG. 6 is a cross-sectional view of a carrier for the drive mechanism of the film cassette holder of the present invention with portions in dotted lines.
Figure 7:
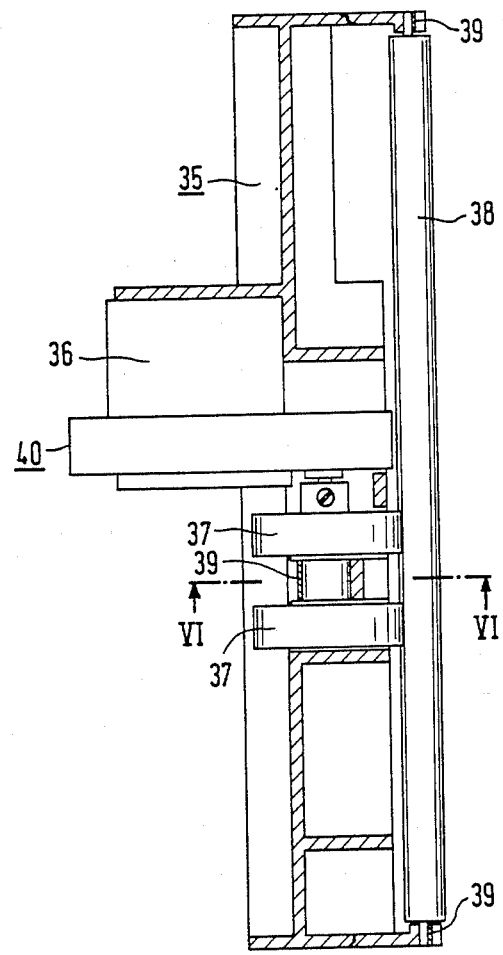
FIG. 7 is a cross-sectional view taken along the lines VII—VII of FIG. 6.

As best illustrated in FIGS. 6 and 7, a carrier part 35 is insertable into a housing part 5a for the acceptance of the complete film cassette drive 40. The film drive 40 comprises an electric motor 36 with gearing, twin rollers 37, which are secured to a drive shaft and two cooperating pressure rollers 38 arranged at a distance therefrom roughly corresponding to the thickness of the film cassette. The twin rollers 37 are provided with rubber or rubber-like surfaces. The cooperating pressure rollers 38 are formed of steel. The spacing formed between the generated surface of the twin rollers 37 and the cooperating pressure rollers 38 is dimensioned so that the flexible film cassette can be transported by friction. Both the twin rollers 37 as well as the two cooperating pressure rollers 38 are mounted by biasing means formed by a spring or elastic element such as leaf spring 39. The overall carrier 35 comprising the drive means 40 is secured to the housing part 5a so that the twin rollers and two cooperating pressure rollers are arranged closely adjacent to the secondary diaphragm 31 of the part 5b and form a triangular arrangement relative thereto. Instead of the twin rollers, a drum held in a rubber elastic ring can also, for example, be provided.

Although various minor modifications may be suggested by those versed in the art, it should be understood that I wish to embody within the scope of the patent granted hereon all such modifications as reasonably and properly come within the scope of my contribution to the art.

I claim:

1. In a dental x-ray diagnostic apparatus for panoramic tomograms, said apparatus comprising a radiation source having an exit slit, a holder for a film cassette, a common carrier, said source and holder being mounted opposite one another on said carrier, first adjacent means for moving the carrier with the source and holder around a subject, said holder having a housing with a first slot-shaped opening through which a film cassette is introducable and withdrable, and means for moving the cassette relative to the x-ray source during exposure as well as relative to at least one diaphragm with a second slot-shaped opening in the housing and arranged in a beam path between the radiation source and cassette, the improvements comprising the film cassette being a flexible film cassette enclosing the film to be exposed, and said means for moving the cassette being an electromotive drive arranged in the housing of the film cassette holder adjacent to the second slot-shaped opening and behind the diaphragm such that, when the housing is positioned for taking a panoramic tomogram, said electromotive drive is in line with both said second slot-shaped opening and said exit slit, said electromotive drive of the means for moving the cassette containing at least one drive member and at least one correspondingly arranged cooperating member, means for biasing at least one of the members towards the other member to frictionally engage the film cassette therebetween and to move it past the second slot-shaped opening.

2. In a dental x-ray diagnostic apparatus according to claim 1, wherein the drive member and cooperating member are roller members.

3. In a dental x-ray diagnostic apparatus according to claim 1 wherein the drive member comprises a pair of twin rollers provided on a drive shaft, said cooperating member comprising two cooperating pressure rollers being mounted for free rotation in the holder adjacent the second slot-shaped opening of the diaphragm.

4. In a dental x-ray diagnostic apparatus according to claim 3, wherein at least each engaging surface of the twin rollers is composed of an elastic rubber material and the cooperating pressure rollers are composed of metal.

5. In a dental x-ray diagnostic apparatus according to claim 4, wherein the cooperating pressure rollers extend over the height of the film cassette.

6. In a dental x-ray diagnostic apparatus according to claim 3, wherein at least the twin rollers of the drive element and the drive motor for the twin rolls are arranged in a carrier part releasably received in a housing of the film cassette holder.

7. In a dental x-ray diagnostic apparatus according to claim 1, wherein the housing of said cassette film holder is composed of two physically separable halves formed by a longitudinal division, one half thereof containing a secondary diaphragm and the other half thereof containing the means for moving.

8. In a dental x-ray diagnostic apparatus according to claim 7, wherein at least the housing half containing the diaphragm is composed of a zinc diecasting.

9. In a dental x-ray diagnostic apparatus according to claim 8 wherein the housing of the film cassette holder is mounted on the c arrier for pivotal movement around a vertically extending axis offset from a center of the carrier.

10. In a dental x-ray diagnostic apparatus according to claim 1, wherein the housing of the film cassette holder is mounted on the carrier for pivotal movement around an axis offset from a center of the carrier.

* * * * *